US012313617B2

(12) United States Patent
Caldona et al.

(10) Patent No.: US 12,313,617 B2
(45) Date of Patent: May 27, 2025

(54) POLYMERIC-COATED ELECTRODES FOR SENSING ANALYTES IN LIQUID AND METHODS OF MAKING THE SAME

(71) Applicant: Mississippi State University, Starkville, MS (US)

(72) Inventors: Eugene B. Caldona, Knoxville, TN (US); David O. Wipf, Starkville, MS (US); Dennis W. Smith, Starkville, MS (US); Summer L Nash, Brandon, MS (US)

(73) Assignee: Mississippi State University, Starkville, MS (US)

( * ) Notice: Subject to any disclaimer, the term of this patent is extended or adjusted under 35 U.S.C. 154(b) by 96 days.

(21) Appl. No.: 17/491,003

(22) Filed: Sep. 30, 2021

(65) Prior Publication Data

US 2022/0099649 A1 Mar. 31, 2022

Related U.S. Application Data

(60) Provisional application No. 63/085,536, filed on Sep. 30, 2020.

(51) Int. Cl.
*G01N 33/18* (2006.01)
*G01N 27/02* (2006.01)
*G01N 27/38* (2006.01)

(52) U.S. Cl.
CPC ....... *G01N 33/1833* (2013.01); *G01N 27/026* (2013.01); *G01N 27/38* (2013.01); *G01N 33/1886* (2013.01)

(58) Field of Classification Search
CPC ................. G01N 33/1833; G01N 33/1886
See application file for complete search history.

(56) References Cited

U.S. PATENT DOCUMENTS

| 4,034,219 A | 7/1977 | Louden |
| 10,620,119 B2 | 4/2020 | Kahn et al. |
| 2007/0190662 A1* | 8/2007 | Baetzold ............... C07C 311/51 436/166 |

(Continued)

FOREIGN PATENT DOCUMENTS

| CN | 107003266 A * | 8/2017 | ............ C08J 3/075 |
| WO | WO-2020225509 A1 * | 11/2020 | ............ G01N 27/38 |

OTHER PUBLICATIONS

Kim, Dong Chung, and Dae Joon Kang. "Molecular recognition and specific interactions for biosensing applications." Sensors 8.10 (2008): 6605-6641 (Year: 2008).*

(Continued)

*Primary Examiner* — Kristina M Deherrera
*Assistant Examiner* — Fatemeh Esfandiari Nia
(74) *Attorney, Agent, or Firm* — Stites & Harbison PLLC; Richard S. Myers, Jr.

(57) ABSTRACT

A sensing device is provided. The sensing device includes a base material comprising metal, metalized polymer, or a combination thereof; a first coating layer over the base material, the first coating layer comprising polystyrene; and a second coating layer over the first coating layer, the second coating layer comprising a fluorinated silane-modified polystyrene. Also provided are a method of making the sensing device and a method of electrochemical detection of an analyte in a liquid using the sensing device.

20 Claims, 1 Drawing Sheet

(56) References Cited

U.S. PATENT DOCUMENTS

| | | | | |
|---|---|---|---|---|
| 2016/0231267 A1* | 8/2016 | Swager | ............... | B82Y 15/00 |
| 2019/0360959 A1* | 11/2019 | Ying | ................. | G01N 33/493 |
| 2021/0285905 A1* | 9/2021 | Hillebrand | ............ | G01N 33/18 |
| 2022/0136990 A1* | 5/2022 | Verschinin | ............ | G01R 27/22 |
| | | | | 702/19 |

OTHER PUBLICATIONS

Wu, Zhen-Lin, et al. "Polymer-based device fabrication and applications using direct laser writing technology." Polymers 11.3 (2019): 553 (Year: 2019).*
Solberg, A. H. S., Remote Sensing of Ocean Oil-Spill Pollution. Proc. IEEE 2012, I 00 (I 0), 2931-2945.
Sabouri, A.; Yetisen, A. K.; Sadigzade, R.; Hassanin, H.; Essa, K.; Butt, H. Three-Dimensional Microstructured Lattices for Oil Sensing. Energy Fuels 2017, 31 (3), 2524-2529.

* cited by examiner

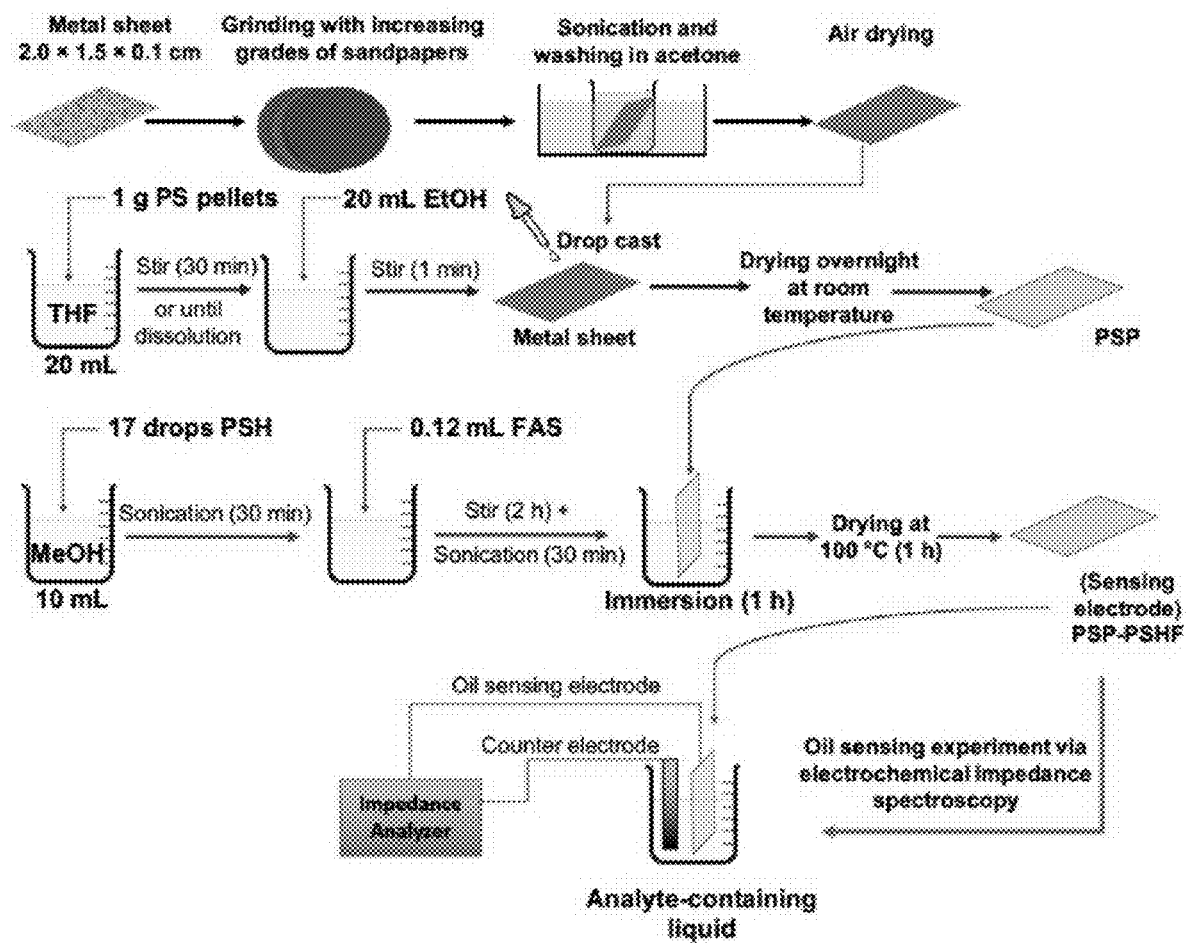

POLYMERIC-COATED ELECTRODES FOR SENSING ANALYTES IN LIQUID AND METHODS OF MAKING THE SAME

RELATED APPLICATIONS

This application claims the benefit of U.S. Provisional Application Ser. No. 63/085,536, filed Sep. 30, 2020, the entire disclosure of which is incorporated herein by this reference.

GOVERNMENT INTEREST

This invention was made with government support under grant number 1659830 awarded by the National Science Foundation INFEWS REU. The government has certain rights in the invention.

TECHNICAL FIELD

The presently-disclosed subject matter relates to articles and methods for sensing analytes in liquids. In particular, certain embodiments of the presently-disclosed subject matter relate to polymeric-coated electrodes for sensing analytes, such as oil, in liquids, and methods of making and using the same.

BACKGROUND

Water and other liquids may be contaminated with oil through a number of different sources, including natural oil seeps, motor vehicles, improper disposal, and accidental spills. Such contamination can be harmful and, in some cases, devastating to the environment. However, conventional and current sensing techniques mainly involve the use of materials that require complicated fabrication and/or electronic devices, which are often expensive and require sophisticated operation, data processing, and analysis methods. Although there have been various attempts to address the need for less expensive monitoring (e.g., U.S. Pat. Nos. 10,620,119; 4,034,219; Solberg, A. H. S., *Remote Sensing of Ocean Oil-Spill Pollution*. Proc. IEEE 2012, 1 00 (I 0), 2931-2945; Sabouri, A.; Yetisen, A. K.; Sadigzade, R.; Hassanin, H.; Essa, K.; Butt, H. Three-Dimensional Microstructured Lattices for Oil Sensing. *Energy Fuels* 2017, 31 (3), 25242529), there remains a need for simpler, more efficient sensing devices and methods.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a sensing device for electrochemical detection or sensing of an analyte in a liquid, the device including a base material comprising metal, metalized polymer, or a combination thereof; a first coating layer over the base material, the first coating layer comprising polystyrene; and a second coating layer over the first coating layer, the second coating layer comprising a fluorinated silane-modified polystyrene. In some embodiments, the fluorinated silane-modified polystyrene is fluoroalkylsilane-modified polystyrene hydroxylate (PSHF). In some embodiments, the analyte is oil. In some embodiments, the analyte is a pathogenic agent. In some embodiments, the liquid is water. In some embodiments, the liquid is an aqueous solution.

Also provided herein, in some embodiments, is a method of making a sensing device, the method including preparing a base material by grinding the base material to form a polished base material, washing and sonicating the polished base material in acetone to form a washed base material, and drying the washed base material for form a prepared base material; forming a first coating solution by mixing and stirring polystyrene and a low boiling point solvent to dissolve the polystyrene and form a first mixture of the first coating solution, and adding at least one polar non-aqueous solvent to the first mixture and stirring to precipitate the polystyrene and form a second mixture of the first coating solution; drop casting the second mixture of the first coating solution onto the base material to create a first coating layer over the base material; drying the first coated base material to form a first dried coating layer over the base material; forming a second coating solution by mixing and sonicating an ionically charged surface chemically functionalized polymer bead and at least one polar non-aqueous solvent to form a first mixture of the second coating solution, adding a fluorinated silane to the first mixture of the second coating solution to form a second mixture of the second coating solution, and stirring and sonicating the second mixture of the second coating solution to form a third mixture of the second coating solution; dip coating and immersing the base material including the first dried coating layer in the third mixture of the second coating solution to form a second coating layer; and drying the second coating layer to form a second dried coating layer over the first dried coating layer.

In some embodiments, the low boiling point solvent is tetrahydrofuran (THF). In some embodiments, the ionically charged surface chemically functionalized polymer bead is polystyrene bead hydroxylate (PSH). In some embodiments, the amount of PSH is 17 drops of a 2.6 wt % suspension in water and wherein each drop is about 31.4 mg of the 2.6 wt % polymer bead suspension in water. In some embodiments, the at least one polar non-aqueous solvent is selected from the group consisting of ethanol, methanol, or a combination thereof. In some embodiments, the fluorinated silane is fluoroalkylsilane. In some embodiments, the base material is metal, metalized polymer, or a combination thereof. In some embodiments, the metal is selected from the group consisting of stainless steel, aluminum, or a combination thereof. In some embodiments, the drying is at room temperature.

Further provided herein, in some embodiments, is a method of electrochemical detection or sensing of an analyte in a liquid, the method including connecting the sensing device and a counter electrode to an impedance analyzer; immersing the sensing device and the counter electrode in the liquid; and detecting the presence or absence of an analyte through electrochemical impedance spectroscopy. In some embodiments, the analyte detected is a pathogenic agent, a toxic agent, a mutagenic agent, or a combination thereof. In some embodiments, the pathogenic agent is an organism, a virus, or a combination thereof. In some embodiments, the analyte detected is oil. In some embodiments, the oil detected is selected from the group consisting of a non-polar chemical hydrophobic, lipophilic, animal, vegetable, petrochemical, volatile substance, non-volatile substance, lipid, fatty acid, biological pathogen, bacteria, virus, and combinations thereof.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description refers to the following drawings, wherein:

FIG. 1 shows a schematic illustrating the process and methodology of forming coated electrodes for detection of oil in aqueous solutions or aqueous mixtures.

DEFINITIONS

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the terms "treatment" or "treating" refer to the medical management of a patient with the intent to heal, cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. For example, in some embodiments treatment refers to the healing bone tissue that is fractured and/or healing wounded skin tissue.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Provided herein are polymeric coatings for analyte detection. In some embodiments, the polymeric coating is a superhydrophobic and/or superoleophobic polymeric coating material. In some embodiments, the polymeric coating includes polystyrene (PS). For example, in one embodiment, the coating includes precipitated PS (PSP). Additionally or alternatively, in some embodiments, the coating includes a fluorinated silane-modified polystyrene. Suitable fluorinated silanes include, but are not limited to, fluoroalkylsilane (FAS; e.g., 1H, 1H, 2H, 2H-perfluorodecyltriethoxysilane, and the like). Suitable polystyrenes include, but are not limited to, polystyrene hydroxylate (PSH). For example, in one embodiment, the coating includes a fluoroalkylsilane-modified polystyrene hydroxylate (PSHF). In some embodiments, the polymeric coating includes at least two polymeric coating layers. For example, in one embodiment, the polymeric coating includes a first PSP layer and a second PSHF layer.

Also provided herein are sensors for detecting analytes in liquids. In some embodiments, the sensors include electrodes comprising the polymeric coating material coated onto a base material. Suitable base materials include, but are not limited to, metals (e.g., stainless steel, aluminum), metallized polymer (e.g., metalized plastic, rubber, or composite), or any other suitable base material for use in a sensor. In some embodiments, the electrode includes the PSP layer coated on the base material. In some embodiments, the electrode includes the PSHF layer coated on the base material. In some embodiments, the electrode includes the PSP layer coated on the base material and the PSHF layer coated over the PSP layer. For example, in one embodiment, the sensor includes a fluoroalkylsilane-modified polystyrene-coated metal electrode. In another embodiment, the sensor includes a fluoroalkylsilane-modified polystyrene-coated metallized plastic electrode.

The coated metal electrodes disclosed herein are strongly repellent to water, highly concentrated strong acids, strong bases, salt solutions, and low-surface-tension liquids like oil. Additionally, the polymeric coatings provide high thermal stability, anti-corrosion, self-cleaning properties, and stable contact angles for oil and water, even with application of a mechanical load. Furthermore, aside from the electrical connections involved during the analyte sensing process, the coating material is simple and does not contain or require any internal electrical circuits. As such, the polymeric coatings and sensors disclosed herein may be used for efficient, inexpensive, and sensitive electrochemical detection of analytes in liquid. Accordingly, further provided herein, are methods of detecting analytes in liquids.

In some embodiments, the method of detecting analytes in liquids includes connecting the polymeric-coated electrode (i.e., sensing electrode) and a counter electrode to an impedance analyzer, immersing the sensing electrode and counter electrode in a liquid, and detecting the presence or absence of an analytes through electrochemical impedance spectroscopy. The electrochemical impedance spectroscopy using the electrodes disclosed herein provides sensitive electrochemical detection of analytes in liquids. Any suitable analyte may be detected using the present method, including, but not limited to, oil or any other analyte that can be detected or sensed (e.g., any substance or chemical constituent that is to be analyzed, identified, and/or measured and that is of interest in an analytical procedure or chemical analysis). Such other analytes include any non-polar chemical hydrophobic, lipophilic, animal, vegetable, petrochemical, volatile, and/or non-volatile substance, or a combination thereof, and including lipids, fatty acids, and biological pathogens that are characteristic of biological pathogens such as bacteria and viruses, for example, or a combination thereof. The analyte detected or sensed may be a pathogenic agent, toxic agent, or mutagenic agent, or a combination thereof. The pathogenic agent detected or sensed may be an organism or a virus, or a combination thereof. The virus detected or sensed may be a corona virus, or derived from a corona virus, and the corona virus detected or sensed may be COVID-19, for example. In some embodiments, the sensor may be designed to detect numerous analytes, such as, for example, oil and pathogens. Similarly, the method may be used to detect the analyte in any suitable liquid, such as, but not limited to, water, an aqueous solution, or an aqueous mixture.

In some embodiments, for example, the method includes immersing a fluoroalkylsilane-modified polystyrene-coated metal electrode in water and detecting the presence of oil through changes in the impedance spectroscopic properties of the coated metals. Due to its superoleophobicity, the coating material merely senses the presence of oil in the water without absorbing the oil. The presence of a minute amount of analyte in the liquid causes detectable changes in the impedance spectroscopic properties of the polymeric-coated electrode. For example, in some embodiments, the sensors and/or coating materials disclosed herein can detect oil in water at concentrations as low as 0.1 wt %. Accordingly, in some embodiments, the method includes monitoring for suspected oil spill incidents. Additionally or alternatively, in some embodiments, the method includes validation of oil/water separation processes and/or confirmation of operational and illegal discharges of oil from ships. Without wishing to be bound by theory, it is believed that the coating material disclosed herein is the first superoleophobic coating material capable of sensing oil in water.

Still further provided herein are methods of making the sensors. In some embodiments, the base material is prepared via polishing by grinding and/or sanding, washing and/or sonicating the polished base material in acetone or suitable solvent, and then drying the washed and sonicated base material. Alternatively, in some embodiments, a prepared base material is obtained prior to coating. The base material is then coated with at least a first coating layer and/or a second coating layer. In some embodiments, coating the base material includes forming a first dried coating layer over the base material, then forming a second dried coating layer over the first dried coating layer. In some embodiments, each dried coating layer is formed in a two-step process involving drop-cast and/or dip coating the polymeric coating material on the base material.

In some embodiments, forming the first dried coating layer includes mixing and stirring polystyrene and a low boiling point solvent, such as tetrahydrofuran, at room temperature, to dissolve the polystyrene and to form a first mixture of a first coating solution. Next, the method includes adding at least one polar non-aqueous solvent, such as ethanol, to the first mixture and stirring to precipitate the polystyrene and form a second mixture of the first coating solution. The second mixture of the first coating solution is then drop casted onto the base material to create a first coating layer on the base material, which is dried to form a first dried coating layer on the base material.

In some embodiments, forming the second dried coating layer includes mixing and sonicating a sufficient amount of ionically charged surface chemically functionalized polymer bead, such as polystyrene bead hydroxylate, and at least one polar non-aqueous solvent, such as methanol, to form a first mixture of a second coating solution. As will be appreciated by those skilled in the art, the polar non-aqueous solvent may be one solvent or a combination of solvents. Next, the method includes adding a fluorinated silane, such as, but not limited to, fluoroalkylsilane, to the first mixture of the second coating solution to form a second mixture of the second coating solution. The second mixture of the second coating solution is then stirred and sonicated to form a third mixture of the second coating solution. The base material including the first dried coating layer is then dip coated and immersed in the third mixture of the second coating solution to form a second coating layer over the first dried coating layer. The second coating layer is then dried to form a second dried coating layer over the first dried coating layer. The base material including the first dried coating layer and the second dried coating layer form a polymeric-coated electrode.

In some embodiments, the coating material may be prepared on small stainless steel and aluminum metal sheets, which can be prepared inexpensively in large scale. Additionally or alternatively, the coating material may be prepared on metallized plastic, further reducing cost. Furthermore, as compared to existing methods which involve complex uses of materials and measurement devices, the coatings, sensors, and methods disclosed herein provide simplicity.

All parameters presented herein including, but not limited to, sizes, dimensions, times, temperatures, pressures, amounts, distances, quantities, ratios, weights, volumes, percentages, and/or similar features and data and the like, for example, represent approximate values and can vary with the possible embodiments described and those not necessarily described but encompassed by the invention. Unless defined otherwise, all technical and scientific terms used herein have the same meaning as commonly understood to one of ordinary skill in the art to which this invention belongs. Further, references to the singular forms "a", "an", and "the" concerning any particular item, component, material, or product include plural references and are defined as at least one and could be more than one, unless the context clearly dictates otherwise. The terminology employed is for the purpose of describing particular embodiments and is not intended to be limiting in any way.

The above detailed description is presented to enable any person skilled in the art to make and use the invention. Specific details have been revealed to provide a comprehensive understanding of the present invention and are used for explanation of the information provided. These specific details, however, are not required to practice the invention, as is apparent to one skilled in the art. Descriptions of specific applications, examples, details, analyses, materials, components, dimensions, and calculations are meant to serve only as representative examples. Various modifications to the preferred embodiments may be readily apparent to one skilled in the art, and the general principles defined herein may be applicable to other embodiments and applications while still remaining within the scope of the invention. Moreover, some features of the invention may be employed without a corresponding use of the other features. There is no intention for the present invention to be limited to the embodiments shown and the invention is to be accorded the widest possible scope consistent with the principles and features disclosed herein.

While various embodiments of the present invention have been described above, it should be understood that they have been presented by way of example and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. The preferred embodiments of the invention have been described herein, but it should be understood that the broadest scope of the invention includes such modifications as additional or different methods and materials. Many other advantages of the invention will be apparent to those skilled in the art from the above descriptions and the subsequent preferred embodiments and/or claims. Thus, the present invention should not be limited by any of the above-described exemplary embodiments.

The compositions, materials, products, processes, apparatus, systems, and methods of the present invention are often best practiced by empirically determining the appropriate values of the operating parameters, or by conducting simulations to arrive at best design for a given application. Accordingly, all suitable modifications, combinations, and equivalents should be considered as falling within the spirit and scope of the invention.

The presently-disclosed subject matter is further illustrated by the following specific but non-limiting examples. The following examples may include compilations of data that are representative of data gathered at various times during the course of development and experimentation related to the presently-disclosed subject matter. Those skilled in the art will recognize, or be able to ascertain, using no more than routine experimentation, numerous equivalents to the specific substances and procedures described herein.

Examples

This Example describes the formation of a novel apparatus for sensing analytes in aqueous solutions or aqueous mixtures. More specifically, this Example discusses a superhydrophobic and/or superoleophobic polymeric coating base material that can be used as a sensor or sensing device for sensing or detecting analyte(s), such as oil, in liquid containing such analyte(s) (i.e., an aqueous solution, an aqueous mixture, or a combination thereof). Also discussed in this Example are methods of detecting analytes using the sensor or sensing device, such as, for example, via electrochemical impedance spectroscopy.

A method of forming a sensing device is illustrated in FIG. 1. To form a base material, 2.0×1.5×0.1 cm metal sheets (e.g., stainless steel, aluminum) were polished until a nearly-mirror finish metal surface was obtained. The metal was polished by grinding and/or sanding to a near-mirror finish with successively finer grades of abrasives and/or polishing compounds. More specifically, the finish was obtained by polishing the metal with increasing grades of sandpaper, for example, 240, 400, and 800 SiC paper grades. The polishing of the base material was followed by a washing and 15-min sonication in acetone or suitable solvent, and air drying of the base material.

Next, the first coating formulation was prepared by completely dissolving 1 g of polystyrene (PS) pellets in 20 mL of a suitable low boiling point solvent, such as tetrahydrofuran (THF). The solution was magnetically stirred at room temperature for 30 min or until complete dissolution of the PS pellets was achieved. An amount of 20 mL of ethanol (EtOH) was slowly added to the solution to precipitate the PS and the solution was further stirred for 1 min. The resulting solution, which contained the precipitated PS (PSP), was drop-casted onto the metal surface base material to form a first coated base material, followed by an overnight drying in air at room temperature to form a first dried coated base material.

To form a second coating formulation, ionically charged functionalized polymer bead, such as 200-nm-sized PS bead hydroxylate (PSH), was added to 10 mL of methanol (MeOH), and the resultant solution was sonicated for 30 min. In this Example, 17 drops of a 2.6 wt % suspension of the polymer bead in water was used. Each drop consisted of about 31.4 mg of the 2.6 wt % polymer bead suspension in water. This amount or quantity of polymer bead drops provided the best superoleophobicity property. An amount of 0.12 mL of a fluorinated silane, such as fluoroalkylsilane (FAS, e.g. 1H, 1H, 2H, 2H-perfluorodecyltriethoxysilane, and the like), was added to the solution, and the resultant solution (PSHF) was magnetically stirred for 2 h at room temperature, followed by sonication for 30 min. The hydroxylate (or functionalized) form of the PS beads provided good chemical affinity with the FAS. The first dried coated base material (PSP-coated metal sheet) was dip-coated and allowed to remain immersed in the PSHF solution for 1 h to form a second coated base material. This was followed by drying of the coated metal (PSP-PSHF) at 100° C. for 1 h in air to form a second dried coated base material formed over the first dried coated base material, all of which combined to form the polymeric-coated electrode sensing device of the invention.

The prepared coated metals are strongly repellent to water, highly concentrated strong acids, strong bases, salt solutions, and low-surface-tension liquids like oil. The coating also displays high thermal stability, anti-corrosion and self-cleaning properties, and stable contact angles for oil and water, even with application of a mechanical load. As such, this coating material is ideal for oil and other analyte sensing, as it can detect amounts as low as about 0.1 wt % oil in water. Accordingly, the polymeric-coated electrode may be used to quickly and efficiently detect the presence of a very small amount of oil in water by electrochemical impedance spectroscopy. This includes, for example, monitoring suspected oil spill incidents and/or efficient validation of oil/water separation processes. As compared to complex materials and measurement devices currently being used, the sensor described herein provides simplicity for analyte detection. Additionally, and without wishing to be bound by theory, this is believed to be the first use of a superoleophobic coating that is capable of sensing oil or analyte in aqueous solutions or aqueous mixtures.

The compositions, materials, products, processes, apparatus, systems, and methods of the present disclosure are often best practiced by empirically determining the appropriate values of the operating parameters, or by conducting simulations to arrive at best design for a given application. Accordingly, all suitable modifications, combinations, and equivalents should be considered as falling within the spirit and scope of the invention.

While the disclosure is susceptible to various modifications and alternative forms, specific embodiments thereof have been shown by way of example in the drawings and are herein described in detail. It should be understood, however, that the description of specific embodiments is not intended to limit the disclosure to cover all modifications, equivalents and alternatives falling within the spirit and scope of the disclosure as defined by the appended claims.

All publications, patents, and patent applications mentioned in this specification are herein incorporated by reference to the same extent as if each individual publication, patent, or patent application was specifically and individually indicated to be incorporated by reference.

What is claimed is:

1. A sensing device for electrochemical detection or sensing of an analyte in a liquid, the device comprising:
    a base material comprising metal, metalized polymer, or a combination thereof;
    a first coating layer over the base material, the first coating layer comprising polystyrene; and
    a second coating layer over the first coating layer, the second coating layer comprising a fluorinated silane-modified polystyrene.

2. The sensing device of claim 1, wherein the fluorinated silane-modified polystyrene is fluoroalkylsilane-modified polystyrene hydroxylate (PSHF).

3. The sensing device of claim 1, wherein the analyte is oil.

4. The sensing device of claim 1, wherein the analyte is a pathogenic agent.

5. The sensing device of claim 1, wherein the liquid is water.

6. The sensing device of claim 1, wherein the liquid is an aqueous solution.

7. A method of making the sensing device of claim 1, the method comprising:
    preparing a base material by:
        grinding the base material to form a polished base material;
        washing and sonicating the polished base material in acetone to form a washed base material; and
        drying the washed base material for form a prepared base material;
    forming a first coating solution by:
        mixing and stirring polystyrene and a low boiling point solvent to dissolve the polystyrene and form a first mixture of the first coating solution; and
        adding at least one polar non-aqueous solvent to the first mixture and stirring to precipitate the polystyrene and form a second mixture of the first coating solution;
    drop casting the second mixture of the first coating solution onto the base material to create a first coating layer over the base material;
    drying the first coated base material to form a first dried coating layer over the base material;
    forming a second coating solution by:
        mixing and sonicating an ionically charged surface chemically functionalized polymer bead and at least one polar non-aqueous solvent to form a first mixture of the second coating solution;
        adding a fluorinated silane to the first mixture of the second coating solution to form a second mixture of the second coating solution; and
        stirring and sonicating the second mixture of the second coating solution to form a third mixture of the second coating solution;
    dip coating and immersing the base material including the first dried coating layer in the third mixture of the second coating solution to form a second coating layer; and
    drying the second coating layer to form a second dried coating layer over the first dried coating layer.

8. The method of claim 7, wherein the low boiling point solvent is tetrahydrofuran (THF).

9. The method of claim 7, wherein the ionically charged surface chemically functionalized polymer bead is polystyrene bead hydroxylate (PSH).

10. The method of claim 9, wherein the amount of PSH is 17 drops of a 2.6 wt % suspension in water and wherein each drop is about 31.4 mg of the 2.6 wt % polymer bead suspension in water.

11. The method of claim 7, wherein the at least one polar non-aqueous solvent is selected from the group consisting of ethanol, methanol, or a combination thereof.

12. The method of claim 7, wherein the fluorinated silane is fluoroalkylsilane.

13. The method of claim 7, wherein the base material is metal, metalized polymer, or a combination thereof.

14. The method of claim 13, wherein the metal is selected from the group consisting of stainless steel, aluminum, or a combination thereof.

15. The method of claim 7, wherein the drying is at room temperature.

16. A method of electrochemical detection or sensing of an analyte in a liquid, the method comprising:
   connecting the sensing device of claim 1 and a counter electrode to an impedance analyzer;
   immersing the sensing device and the counter electrode in the liquid; and
   detecting the presence or absence of an analyte through electrochemical impedance spectroscopy.

17. The method of claim 16, wherein the analyte detected is a pathogenic agent, a toxic agent, a mutagenic agent, or a combination thereof.

18. The method of claim 17, wherein the pathogenic agent is an organism, a virus, or a combination thereof.

19. The method of claim 16, wherein the analyte detected is oil.

20. The method of claim 19, wherein the oil detected is selected from the group consisting of a non-polar chemical hydrophobic, lipophilic, animal, vegetable, petrochemical, volatile substance, non-volatile substance, lipid, fatty acid, biological pathogen, bacteria, virus, and combinations thereof.

* * * * *